US007288383B2

(12) United States Patent
Ye et al.

(10) Patent No.: US 7,288,383 B2
(45) Date of Patent: Oct. 30, 2007

(54) EOSINOPHIL-DERIVED NEUROTOXIN AS A MARKER FOR OVARIAN CANCER

(75) Inventors: Bin Ye, Brookline, MA (US); Daniel W. Cramer, Chestnut Hill, MA (US); Samuel C. Mok, Brookline, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 392 days.

(21) Appl. No.: 10/755,854

(22) Filed: Jan. 13, 2004

(65) Prior Publication Data

US 2004/0157251 A1 Aug. 12, 2004

Related U.S. Application Data

(60) Provisional application No. 60/440,029, filed on Jan. 15, 2003.

(51) Int. Cl.
*G01N 33/53* (2006.01)
*C12Q 1/00* (2006.01)

(52) U.S. Cl. ........................................... 435/7.1; 435/4

(58) Field of Classification Search .................. 435/7.1
See application file for complete search history.

(56) References Cited

U.S. PATENT DOCUMENTS

| | | | | |
|---|---|---|---|---|
| 5,604,106 | A | 2/1997 | Liotta et al. | 435/7.23 |
| 5,695,761 | A | 12/1997 | Denhardt et al. | 424/184.1 |
| 5,712,104 | A | 1/1998 | Yamamoto | 435/7.92 |
| 5,801,004 | A | 9/1998 | Hudson et al. | 435/7.23 |
| 5,866,119 | A | 2/1999 | Bandman et al. | 424/94.6 |
| 5,928,883 | A * | 7/1999 | Gleich et al. | 435/7.21 |
| 6,414,219 | B1 | 7/2002 | Denhardt et al. | 800/18 |
| 6,675,104 | B2 | 1/2004 | Paulse et al. | 702/22 |
| 6,686,444 | B2 | 2/2004 | Ashkar | 530/329 |
| 2002/0039753 | A1 | 4/2002 | Chai et al. | 435/7.23 |
| 2002/0052308 | A1 | 5/2002 | Rosen et al. | 514/1 |
| 2003/0087250 | A1 | 5/2003 | Monahan et al. | 435/6 |

OTHER PUBLICATIONS

Tockman et al (Cancer Res., 1992, 52:2711s-2718s).*

Brakora, et al., "Utility of Osteopontin as a Biomarker in Recurrent Epithelial Ovarian Cancer," *Gynoecologic Oncology 93*:361-365 (2004).

Furger, et al., "The Functional and Clinical Roles of Osteopontin in Cancer and Metastasis," *Curr. Mol. Med. 1*:621-632 (2001).

Schorge, et al., "Osteopontin as an Adjunct to CA125 in Detecting Recurrent Ovarian Cancer," *Clin. Cancer Res. 10*:3474-3478 (2004).

Bast et al., "A Radioimmunoassay Using a Monoclonal Antibody to Monitor the Course of Epithelial Ovarian Cancer," *N. Engl. J. Med. 309*:883-887 (1983).

Berteau, et al., "Prostasin mRNA to Detect Prostate Cells in Blood of Cancer Patients,", *Clin. Chem. Lab. Med. 37*:S119 (1999).

Chen, et al., "Down-Regulation of Prostasin Serine Protease: A Potential Invasion Suppressor in Prostate Cancer," *Prostate 48*:93-103 (2001).

Chen, et al., "Prostasin Serine Protease Inhibits Breast Cancer Invasiveness and Is Transcriptionally Regulated by Promoter DNA Methylation," *Int. J. Cancer 97*:323-329 (2002).

Cheung, et al., "Identify Metastasis-Associated Genes in Hepatocellular Carcinoma through Clonality Delineation for Multinodular Tumor," *Cancer Res. 62*:4711-4621 (2002).

Coolen, et al., "Elevation of Brain-Type Creatine Kinase in Serum from Patients with Carcinoma," *Cancer 44*:1414-1418 (1979).

Cramer, et al., "Carotenoids, Antioxidants and Ovarian Cancer Risk in Pre- and Postmenopausal Women," *Int. J. Cancer 94*:128-134 (2001).

Daly, et al., "The Search for Predictive Patterns in Ovarian Cancer: Proteomics Meets Bioinformatics," *Cancer Cell 1*:111-112 (2002).

Denhardt, et al., "Osteopontin: A Protein with Diverse Functions," *FASEB J. 7*:1475-1482 (1993).

DeRisi, et al., "Use of cDNA Microarray to Analyse Gene Expression Patterns in Human Cancer," *Nature Genetics 14*:457-460 (1996).

Fish, et al., "Changes in Serum Actue Phase Proteins in Ovarian Cancer Patients Receiving Cis-Diamminedichloro-platinum (CDDP) Infusion Therapy," *Clinical Biochem. 17*:39-41 (1984).

Fish, et al., "Serum Haptoglobin and α1-Acid Glycoprotein as Indicators of the Effectiveness of *cis*-Diamminedichloroplatinum (CDDP) in Ovarian Cancer Patients—a Preliminary Report," *Eur. J. Cancer Clin. Oncol. 20*:625-630 (1984).

Giachelli, et al., "Molecular and Cellular Biology of Osteopontin," *Trends Cardiovasc. Med. 5*:88-95 (1995).

Gingrich, et al., "Metastatic Prostate Cancer in a Transgenic Mouse," *Cancer Res. 56*:4096-4102 (1996).

Harvey, et al., "Cancer Cells Release a Covalent Complex Containing Disulfide-Linker Domains from Urinary Plasminogen Activator, Neural Cell Adhesion Molecule, and Haptoglobin α and β Chains," *Arch. Biochem. Biopys. 345*:289-298 (1997).

Heid, et al., "Real Time Quantitative PCR," *Genome Res. 6*:986-994 (1996).

Hooper, et al., "Testisin, a New Human Serine Proteinase Expressed by Premeiotic Testicular Germ Cells and Lost in Testicular Germ Cell Tumors," *Cancer Res. 59*:3199-3205 (1999).

Hooper, et al., "Localization, Expression and Genomic Structure of the Gene Encoding the Human Serine Protease Testisin," *Biochimica et Biophysica Acta 1492*:63-71 (2000).

Kibel, et al., "Loss of Heterozygosity at 12P12-13 in Primary and Metastatic Prostate Adenocarcinoma," *J. Urol. 164*:192-196 (2000).

Kiefer, et al., "The cDNA and Derived Amino Acid Sequence for Human Osteopontin," *Nuc. Ac. Res. 17*:3306 (1989).

(Continued)

*Primary Examiner*—Misook Yu
*Assistant Examiner*—Sean E. Aeder
(74) *Attorney, Agent, or Firm*—Michael A. Sanzo; Law Office of Michael A. Sanzo, LLC

(57) ABSTRACT

The present invention is directed to methods of identifying women at increased risk of having ovarian cancer. Identification is based upon the extent to which biological samples derived from the women exhibit elevated levels of eosinophil-derived neurotoxin (EDN).

5 Claims, 3 Drawing Sheets

OTHER PUBLICATIONS

Kim, et al., "Osteopontin as a Potential Diagnostic Biomarker for Ovarian Cancer," *JAMA* 287:1671-1679 (2002).
Ko, et al., "Haptoglobin Typing and Quantitation in Normal Chinese Females and Gynecologic Cancer Patients," *Chinese J. Microbiol. Immunol.* 13:149-157 (1980).
Ko, et al., "Haptoglobin Typing and Quantitation in Normal Chinese Females and Gynecologic Cancer Patients," *Chinese J. Microbiol. Immunol.* 13:149-157 (1980) Abstract; Database Medline, Accession No. 81089629.
Kurtz, et al., "Serum Creatine Kinase BB Isoenzyme as a Diagnostic Aid in Occult Small Cell Lung Cancer," *Cancer* 56:562-566 (1985).
Mills, et al., "Future for Ovarian Cancer Screening: Novel Markers From Emerging Technologies of Transcriptional Profiling and Proteomics," *J. Natl. Cancer. Inst.* 93:1437-1439 (2001).
Mok, et al., "Prostasin, a Potential Serum Marker for Ovarian Cancer: Identification Through Microarray Technology," *J. Natl. Cancer Inst.* 93:1458-1464 (2001).
Mok, et al., "Molecular Cloning of Differentially Expressed Genes in Human Epithelial Ovarian Cancer," *Gynecologic Oncol.* 52:247-252 (1994).
Mok, et al., "SPARC, an Extracellular Matrix Protein with Tumor-Suppressing Activity in Human Ovarian Epithelial Cells," *Oncogene* 12:1895-1901 (1996).
Müeller-Pillasch, et al., "Cloning of a Gene Highly Overexpressed in Cancer Coding for a Novel KH-Domain Containing Protein," *Oncogene* 14:2729-2733 (1997).
Oldberg, et al., "Cloning and Sequence Analysis of Rat Bone Sialoprotein (Osteopontin) cDNA Reveals an Arg-Gly-Asp Cell-Binding Sequence," *Proc. Natl. Acad. Sci. USA* 83:8819-8823 (1986).
Oldberg, et al., "Identification of a Bone Sialoprotein Receptor in Osteosarcoma Cells," *J. Biol. Chem.* 263:19433-19436 (1988).
Patarca, et al., "Differential Induction of Interferon γ Gene Expression after Activation of CD4+ Cells by Conventional Antigen and Mls Superantigen," *Proc. Natl. Acad. Sci. USA* 88:2736-2739 (1991).
Peng, et al., "Proteomics: The Move to Mixtures," *J. Mass Spectrom.* 36:1083-1091 (2001).
Petricoin, et al., "Use of Proteomic Patterns in Serum to Identify Ovarian Cancer," *Lancet* 359:572-577 (2002).
Piva, et al., "Interleukin-6 Differentially Stimulates Haptoglobin Production by Peritoneal and Endometriotic Cells in Vitro: A Model for Endometrial-Peritoneal Interaction in Endometriosis," *J. Clin. Endocrinol. Metab.* 86:2553-2561 (2001).
Ren, et al., "Reduced Lysyl Oxidase Messenger RNA Levels in Experimental and Human Prostate Cancer," *Cancer Res.* 58:1285-1290 (1998).
Schneider, et al., "Osteopontin But Not Osteonectin Messenger RNA Expression Is a Prognostic Marker in Curatively Resected Non-Small Cell Lung Cancer," *Clin. Cancer Res.* 10:1588-1596 (2004).
Schriml, et al., "Tyramide Signal Amplification (TSA)-FISH Applied to Mapping PCR-Labeled Probes Less Than 1 kb in Size," *BioTechniques* 27:608-613 (1999).
Schummer, et al., "Comparative Hybridization of an Array of 21 500 Ovarian cDNAs for the Discovery of Genes Overexpressed in Ovarian Carcinomas," *Gene* 238:375-385 (1999).
Senger, et al., "Elevated Expression of Secreted Phosphoprotein I (Osteopontin, 2ar) as a Consequence of Neoplastic Transformation," *Anticancer Res.* 9:1291-1300 (1989).
Sharp, et al., "Tumor Cells Are the Source of Osteopontin and Bone Sialoprotein Expression in Human Breast Cancer," *Lab. Investing.* 79:869-877 (1999).
Shindo, "Haptoglobin Subtyping with Anti-Haptoglobin.Alpha. Chain Antibodies," *Electrophoresis* 11:483-488 (1990), see especially Abstract; Database Caplus, Accession No. 1990:548290, (Sch. Med. Akita Univ., Hondo, Japan.
Smith, et al., "Molecular Cloning of a Tumor Promoter-Inducible mRNA Found in JB6 Mouse Epidermal Cells: Induction Is Stable at High, but Not at Low, Cell Densities," *J. Cell. Biochem.* 34:13-22 (1987).
Szala, et al., "Molecular Cloning of cDNA for the Carcinoma-Associated Antigen GA733-2," *Proc. Natl. Acad. Sci. USA* 87:3542-3546 (1990).
Thompson, et al., "Increased Fucosylation and Other Carbohydrate Changes in Haptoglobin in Ovarian Cancer," *Cancer Letters* 66:43-48 (1992).
Tuck, et al., "Osteopontin Induces Increased Invasiveness and Plasminogen Activator Expression of Human Mammary Epithelial Cells," *Oncogene* 18:4237-4246 (1999).
Vlahou, et al., "Development of a Novel Proteomic Approach for the Detection of Transitional Cell Carcinoma of the Bladder in Urine," *Am. J. Pathol.* 158:1491-1502 (2001).
Wang, et al., "Monitoring Gene Expression Profile Changes in Ovarian Carcinomas Using cDNA Microarray," *Gene* 229:101-108 (1999).
Ye, et al., "Identification and Validation of Urinary Biomarkers for Early Stage of Ovarian Cancer by Multiple Proteomic Approaches," *Proc. Am. Assoc. Cancer Res.* 45:915 (abstract 3964 (2004)).
Yiu, et al., "Prostasin, a Potential Serum Marker for the Early Detection of Ovarian Cancer," *Proceedings of the American Association for Cancer Research Annual* 42:744 (2001).
Yu, et al., "Prostasin Is a Novel Human Serine Proteinase from Seminal Fluid," *J. Biol. Chem.* 269:18843-18848 (1994).
Yu, et al., "Molecular Cloning, Tissue-Specific Expression, and Cellular Localization of Human Prostasin mRNA," *J. Biol. Chem.* 270:13483-13489 (1995).
Zhau, et al., "Biomarkers Associated with Prostate Cancer Progression," *J. Cell. Biochem. Supp.* 19:208-216 (1994).
Ali, et al., "Intercellular Cell Adhesion Molecule-1, Vascular Cell Adhesion Molecule-1, and Regulated on Activation Normal T Cell Expressed and Secreted Are Expressed by Human Breast Carcinoma Cells and Support Eosinophil and Activation," *Am. J. Path.* 157:313-321 (2000).
Alper, "Turning Sweet on Cancer," *Science* 301:159-160 (2003).
Barker, et al., "Eosinophil Cationic Protein cDNA, Comparison with Other Toxic Cationic Proteins and Ribonucleases," *J. Immunol.* 143:952-955 (1989).
Beintema, et al., "Amino Acid Sequence of the Nonsecretory Ribonuclease of Human Urine," *Biochemistry* 27:4530-4538 (1988).
Blumenthal, et al., "Degranulating Eosinophils in Human Endometriosis," *Am. J. Path.* 156:1581-1855 (2000).
Dorta, et al., "Tumour-Associated Tissue Eosinophilia as a Prognostic Factor in Oral Squamous Cell Carcinomas," *Histopathology* 41:152-157 (2002).
Fernández-Aceñero, et al., "Prognostic Influence of Tumor-Associated Eosinophilic Infiltrate in Colorectal Carcinoma," *Cancer* 88:1544-1548 (2000).
Hakomori, "Glycosylation Defining Cancer Malignancy: New Wine in an Old Bottle," *Proc. Natl. Acad. Sci. USA* 99:10231-10233 (2002).
Hamann, et al., "Sequence of Human Eosinophil-Derived Neurotoxin cDNA: Identity of Deduced Amino Acid Sequence with Human Nonsecretory Ribonucleases," *Gene* 83:161-167 (1989).
Hamann, et al., "Structure and Chromosome Localization of the Human Eosinophil-Derived Neurotoxin and Eosinophil Cationic Protein Genes: Evidence for Intronless Coding Sequences in the Ribonuclease Gene Superfamily," *Genomics* 7:535-546 (1990).
Kakugawa, et al., "Up-Regulation of Plasma Membrane-Associated Ganglioside Sialidase (Neu3) in Human Colon Cancer and Its Involvement in Apoptosis Suppression," *Proc. Natl. Acad. Sci. USA* 99:10718-10723 (2002).
Kodama, et al., "Large Cell Carcinoma of the Lung Associated With Marked Eosinophilia," *Cancer* 54:2313-2317 (1984).
Pastrňák, et al., "Local Eosinophilia in Stroma of Tumors Related to Prognosis," *Neoplasma* 31:323-326 (1984).
Rosenberg, et al., "Molecular Cloning of the Human Eosinophil-Derived Neurotoxin: A Member of the Ribonuclease Gene Family," *Proc. Nat. Acad. Sci. USA* 86:4460-4464 (1989).
Sakakibara, et al., "Putative Mouse Oocyte Maturation Inhibitory Protein from Urine of Pregnant Women: N-Terminal Sequence Homology with Human Nonsecretory Ribonuclease," *Chem. Pharm. Bull.* 39:146-149 (1991).

Sakakibara, et al., "Characterization of a Unique Nonsecretory Ribonuclease from Urine of Pregnant Women," *J. Biochem.* 111:325-330 (1992).

Samoszuk, et al., "New Marker for Blood Vessels in Human Ovarian and Endometrial Cancers," *Clin. Cancer Res.* 2:1867-1871 (1996).

Samoszuk, et al., "Occult Deposition of Eosinophil Peroxidase in a Subset of Human Breast Carcinomas," *Am. J. Pathol.* 148:701-706 (1996).

Samoszuk, "Eosinohils and Human Cancer," *Histol, Histopathol.* 12:807-812 (1997).

Schleich, et al., "Serum Ribonuclease Activity in Patients with Ovarian Tumors," *Eur. J. Gynaec. Oncol.* 7:76-81 (1986).

Schleich, et al., "Ovarian Carcinoma: Increase in Clinical Validity by Simultaneous Determination of SRA and CA 125," *J. Cancer Res. Clin. Oncol.* 113:603-607 (1987).

Schwartz, "The Hypereosinophilic Syndrome and the Biology of Cancer," *N. Engl. J. Med.* 348:1199-1200 (2003).

Sheid, et al., "Plasma Ribonuclease, A Marker for the Detection of Ovarian Cancer," *Cancer* 39:2204-2208 (1977).

Suster, "Tumors of the Skin Composed of Large Cells with Abundant Eosinophilic Cytoplasm," *Semin. Diagn. Pathol.* 16:162-177 (1999).

Ye, et al., "Haptoglobin-$\alpha$ Subunit as Potential Serum Biomarker in Ovarian Cancer: Identification and Characterization Using Proteomic Profiling and Mass Spectrometry," *Clin. Cancer Res.* 9:2904-2911 (2003).

\* cited by examiner

MVPKLFTSQI CLLLLLGLLA VEGSLHVKPP QFTWAQWFET

QHINMTSQQC TNAMQVINNY QRRCKNQNTF LLTTFANVVN

VCGNPNMTCP SNKTRKNCHH SGSQVPLIHC NLTTPSPQNI

SNCRYAQTPA NMFYIVACDN RDQRRDPPQY PVVPVHLDRI

```
  1 gctgccctg aaccccagaa caaccagctg gatcagttct cacaggagct acaggccgga
 61 gactgggaaa catggttcca aaactgttca cttcccaaat ttgtctgctt cttctgttgg
121 ggcttctggc tgtggagggc tcactccatg tcaaacctcc acagtttacc tgggctcaat
181 ggtttgaaac ccagcacatc aatatgacct cccagcaatg caccaatgca atgcaggtca
241 ttaacaatta tcaacggcga tgcaaaaacc aaaatacttt ccttcttaca acttttgcta
301 acgtagttaa tgtttgtggt aacccaaata tgacctgtcc tagtaacaaa actcgcaaaa
361 attgtcacca cagtggaagc aggtgcctt aatccactg taacctcaca actccaagtc
421 cacagaatat ttcaaactgc aggtatgcgc agacaccagc aaacatgttc tatatagttg
481 catgtgacaa cagagatcaa cgacgagacc ctccacagta tccggtggtt ccagttcacc
541 tggatagaat catctaagct cctgtatcag cactcctcat catcactcat ctgccaagct
601 cctcaatcat agccaagatc ccatctctcc atatactttg ggtatcagca tctgtcctca
661 tcagtctcca taccccttca gctttcctga gctgaagtgc cttgtgaacc tgcaataaa
721 ctgctttgca aattc
```

Figure 2

EOSINOPHIL-DERIVED NEUROTOXIN AS A MARKER FOR OVARIAN CANCER

CROSS REFERENCE TO RELATED APPLICATIONS

This application claims priority to U.S. provisional application No. 60/440,029, filed on Jan. 15, 2003, which is incorporated in its entirety herein by reference.

STATEMENT OF GOVERNMENT SUPPORT

The work leading to this invention was supported by one or more grants from the U.S. Government. The U.S. Government therefore has certain rights in the invention.

FIELD OF THE INVENTION

The present invention is in the field of tumor cell markers and is particularly concerned with methods of detecting cancer by assaying samples for eosinophil-derived neurotoxin (EDN). In its most preferred embodiment, the invention is directed to methods in which urine samples obtained from a woman are assayed for EDN to determine her risk of either having or developing ovarian cancer.

BACKGROUND OF THE INVENTION

Approximately 70% of women with ovarian cancer are not diagnosed until the disease has reached an advanced stage, i.e., until it has spread to the upper abdomen (stage III) or beyond (stage IV). The five-year survival rate for such women is only about 15%-20%. In contrast, the five-year survival rate for patients diagnosed with stage I disease is close to 90%. Thus, an assay for screening women for early stage disease would be of great benefit.

Unfortunately, the diagnostic tests presently available for ovarian cancer are not well suited to patient screening. For example, serum levels of the tumor marker CA 125 are elevated in the majority of women with stage III or stage IV cancer, but in less than half of the women with stage I disease. In addition, there are many factors unrelated to ovarian cancer that also result in elevated serum levels of CA 125 and which can produce false positives. Attempts to use other assays, either alone or in combination with the CA 125 test, have met with only limited success.

In the late 1970's, Scheid proposed that serum RNase activity might be correlated with ovarian cancer (Scheid, et al., *Cancer* 39:2204 (1977)). Subsequent studies confirmed this relationship and it was suggested that RNase activity could be used as a diagnostic tool, either alone or in conjunction with the CA 125 test (Schleich, et al., *Eur. J Gynaec. Oncol.* 7:76-81 (1986); Schleich, et al., *Cancer Res. Clin. Oncol.* 113:603-607 (1987)). However, one problem with using total RNase activity as a diagnostic marker is that the levels of this enzyme tend to be elevated in many non-cancerous conditions. As a result, attempts have been made to identify particular RNase enzymes that are more specific for cancer (see, e.g., U.S. Pat. No. 5,866,119).

An RNase enzyme that appears to play an important role in inflammatory and allergic diseases is eosinophil-derived neurotoxin (EDN). The sequence for both the human EDN gene and protein have been reported and comparisons have been made with other ribonucleases (Rosenberg, et al., *Proc. Nat'l Acad. Sci. USA* 86:4460-4464 (1989); Hamann, et al., *Gene* 83:162-167 (1989); Hamann, et al., *Genomics* 7:535-546 (1990); Barker, et al., *J. Immunol.* 143:952-955-(1989); and Beintema, et al., *Biochemistry* 27:4530-4533 (1988)). Immunoassays for EDN have been developed and used in the diagnosis of inflammatory bowel disease (U.S. Pat. No. 5,928,883). In addition, an ELISA kit for measuring human EDN is commercially available (Medical and Biological Laboratories Co., Ltd., Watertown, Mass.). Although this enzyme has been extensively studied, there do not appear to have been any reports suggesting that it may be used in helping to diagnose ovarian cancer.

SUMMARY OF THE INVENTION

The present invention is based upon experiments in which surface enhanced laser desorption/ionization (SELDI) mass spectrometry was used to examine urine specimens from women diagnosed as having ovarian cancer. The results were compared with those derived from urine specimens from women with either benign gynecological disease or from subjects without known disease. Using this technique, a protein was identified that was elevated in 60% of patients with ovarian cancer, but in only 29% of patients with non-cancerous ovarian disease and in 18% of disease-free individuals. Sequence analysis was then performed and the protein was identified as EDN.

In its first aspect, the invention is directed to a method of screening a human female subject for the presence of an abnormal ovarian growth (e.g., a benign or malignant tumor) and to therefore determine whether she is at increased risk of having ovarian cancer relative to the general population. This is accomplished by removing a biological sample from the subject and then assaying it to determine the amount of EDN present. The results obtained are compared with those from control samples derived from either the general population or from subjects believed to be free of ovarian cancer. A conclusion is drawn that the test subject has, or is at a high risk of developing, ovarian cancer if the amount of EDN in the test biological sample is significantly higher than the amount in the control samples.

Standard clinical methods may be used for obtaining biological samples with the most preferred sample being urine. Alternatively, blood or plasma may be used in assays or assays may be performed on fluid or tissue derived from the ovary of a patient. Controls may be selected using methods that are well known in the art. Once a level has become well established for the control population, assay results from test biological samples can be directly compared with these known levels. Women identified as being at increased risk would then undergo further clinical evaluation to confirm that an abnormal ovarian growth is present and to determine whether the growth is malignant or benign.

Any method for assaying EDN levels is compatible with the present invention. However, the most preferred method is immunoassay, e.g., a radioimmunoassay or an ELISA. As discussed further in the Examples section, SELDI mass spectrometry can also be used to determine whether EDN levels are elevated. A "significantly elevated" amount of EDN, for the purposes of the present invention, means that the concentration in the test biological sample is higher than the concentration in the control population to a degree that is statistically significant using standard scientific criteria. In general, a test subject would be considered as being at "increased risk" of having or developing ovarian cancer if the amount of EDN present in the test biological sample is at least 20% higher than that seen in the control samples and the likelihood would increase as the difference became more pronounced, e.g., as it rose above 40%, 60% or 80%. Of particular concern would be women showing an elevation of fivefold, tenfold or more.

As discussed above, assays of EDN levels provide a good indication of whether a female subject has a benign or malignant growth of the ovary. One way of distinguishing patients with malignant growths from those with benign growths is based upon the form of EDN present. Specifically, EDN in patients with ovarian cancer is more heavily dimerized and the dimers are more heavily glycosylated than in patients with benign growths. Thus, by comparing the amount of EDN dimer present in a sample to the amount of monomer present, a determination can be made as to whether a subject has a benign or a malignant growth. If quantitation is based on protein, then a ratio of $D_p/M_p$, where Dp=EDN dimer protein and Mp=EDN monomer protein, of less than about 2 is indicative of a subject with a benign growth and a ratio of 2 or greater is indicative of a patient with a malignant growth. If quantitation is based upon glycosylation, then a ratio of Dg/Mg, where Dg=glycosylation associated with EDN dimer and Mg=glycosylation associated with EDN monomer, of about 0.5-1.5 would be indicative of a benign growth. A ration of greater than 3 would indicate the presence of a malignancy. Any method for evaluating dimer and monomer levels is compatible with the invention. One method that has been found to be effective is to immune precipitate EDN from a sample, separate proteins by electrophoresis, perform a western blot and then stain for either protein or glycosylation. Monomeric EDN should migrate in gels with an apparent molecular weight of about 17 kDa and dimers with an apparent molecular weight of about 35 kDa.

It should also be possible to distinguish between a sample from a patient with a benign growth and a sample from a patient with a malignant growth based upon the total amount of glycosylation associated with EDN, i.e., glycosylation associated with all forms of EDN combined. Specifically, EDN glycosylation in a sample from a patient with ovarian cancer should be significantly greater than in a control sample or group of sample derived from one or more patients with a benign ovarian growth. The term "significantly greater" means greater to a degree that is statistically significant using accepted standards of analysis in the art. For example, samples derived from patients with ovarian malignancies might have a total amount of glycosylation that is at least 20% or 40% greater than that in samples derived from patients with benign growths. The main advantage of this method is that it eliminates the need to separate dimeric forms of EDN from monomeric forms.

Although the EDN assays discussed above may be used alone as a screening tool for ovarian cancer, these assays may also be combined with other diagnostic tests for ovarian cancer. In particular, the CA 125 assay may be performed in conjunction with the EDN assay. Patients showing both elevated EDN levels and elevated CA 125 levels would need to be further examined for the presence of tumors and/or closely monitored for signs of neoplastic disease. The EDN assay may also be used as part of a more comprehensive screening procedure in which assays for one or more markers of other cancers or for other diseases are performed. Markers evaluated may include prostate specific antigen, BRCA-1 or BRCA-2.

In addition to using EDN assays as part of a general screening procedure, the assays may also be used more selectively to monitor women already identified as being at high risk for developing ovarian cancer, for example, women in which ovarian cancer is very prevalent in their family history.

Although EDN is good marker for ovarian cancer, it is expected that other types of cancer will also correlate with elevated levels of this protein. Such cancers include, but are not limited to: adenocarcinoma; leukemia; lymphoma; melanoma; myeloma; sarcoma; and teratocarcinoma. Particular organs affected may include the adrenal gland, bladder, bone, bone marrow, brain, breast, cervix, gall bladder, colon, stomach, heart, kidney, liver, lung, muscle, pancreas, parathyroid, prostate, thyroid and uterus. In each case, the same biological assays discussed above would be applied to identify patients with an elevated risk of having or developing the disease.

BRIEF DESCRIPTION OF THE DRAWINGS

FIG. 1: EDN amino acid sequence. FIG. 1 shows the amino acid sequence of human EDN (SEQ ID NO: 1). As discussed herein, this protein has been found to be elevated in patients with ovarian cancer.

FIG. 2: EDN gene sequence. FIG. 2 shows the nucleotide sequence of the human gene coding for EDN (SEQ ID NO:2). Both this sequence and the corresponding amino acid sequence shown in FIG. 1 have been reported in the GenBank database under accession number P10153.

DETAILED DESCRIPTION OF THE INVENTION

Figure 3:
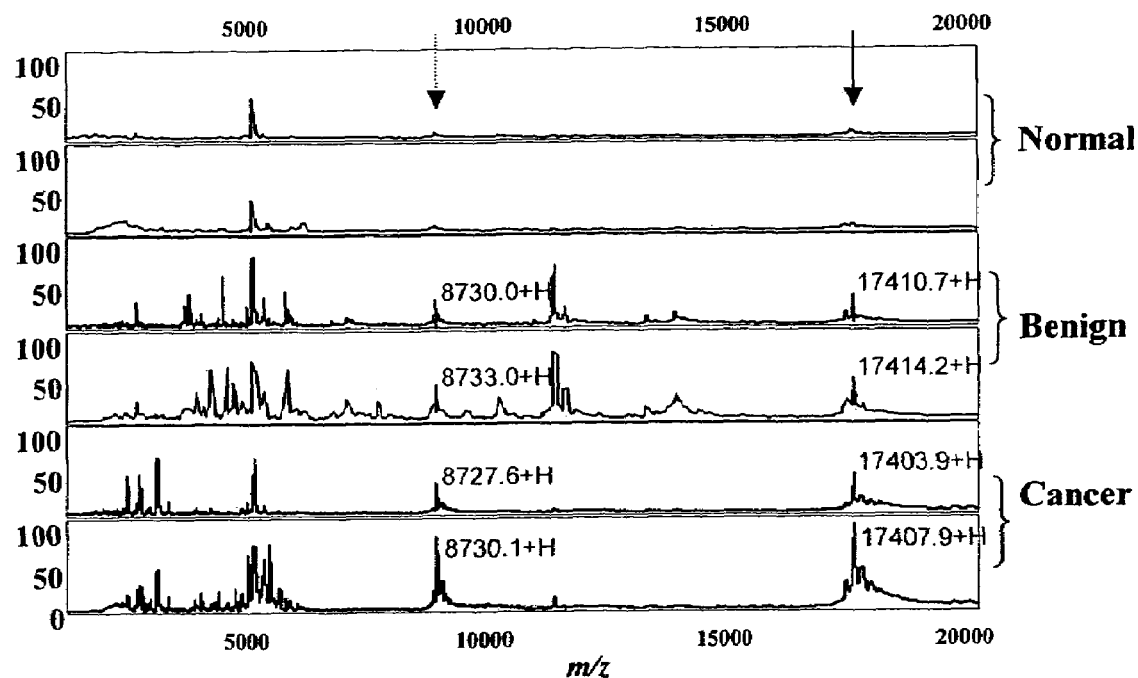
FIG. 3: Urine cationic protein profiling with SELDI-MS. Urine protein profiles between 1,000 and 20,000 were displayed according to mass to charge ratio (m/z). The peaks of interest at 8700 Da (dashed arrow) and 17400 Da (solid arrow) were prevalent in ovarian benign tumor and cancer patients, but to a much lesser extent in normal healthy women.

The present invention is based upon the discovery that one particular RNase enzyme is selectively elevated in patients with ovarian cancer. This enzyme is structurally distinct from other RNases that have been associated with cancer (see, e.g., U.S. Pat. No. 5,866,119) and is not usually elevated in patients that do not have neoplastic disease. The amino acid sequence of the protein is shown in FIG. 1 and contains a segment near its C terminal end which is of particular value in distinguishing it from other members of the RNase family. The segment is 15 residues in length and reads: RDPPQYPVVPVHLDR (SEQ ID NO:3). Peptides having this sequence may be synthesized and used in the generation of antibodies that bind specifically to EDN.

For the purpose of the present invention, antibodies that bind specifically are defined as those that have at least a 100 fold greater affinity for EDN than for other distinct RNases that have been described in the art. The process for producing such antibodies may involve either injecting the peptide into an appropriate animal or injecting peptides that have been conjugated to a protein that increases the immune response. Methods for making and detecting antibodies are well known to those of skill in the art as evidenced by standard reference works such as: Harlow, et al., *Antibodies, Laboratory Manual* Cold Spring Harbor Laboratory, NY (1988); Kennett, et al., *Monoclonal Antibodies and Hybridomas: A New Dimension in Biological Analyses* (1980); and Campbell, "Monoclonal Antibody Technology," in *Laboratory Techniques in Biochemistry and Molecular Biology* (1984).

Although the use of polyclonal antibodies is compatible with the present invention, monoclonal antibodies are generally expected to give greater specificity. These may be prepared using hybridoma technology well known in the art (Kohler, et al., *Nature* 256:495 (1975)). In general, this technology involves immunizing an animal, usually a mouse, with antigen, e.g., the 15 amino acid peptide described above. The splenocytes of the immunized animals are extracted and fused with suitable myeloma cells, e.g., $SP_2O$ cells. After fusion, the resulting hybridoma cells are selectively maintained in HAT medium and then cloned by limiting dilution (Wands, et al., *Gastroenterology* 80:225-232 (1981)). The cells obtained through such selection are then assayed to identify clones which secrete antibodies capable of specifically binding to EDN.

The antibodies of the present invention may be used to detect the presence of EDN in any of a variety of immunoassays. For example, the antibodies may be used in radioimmunoassays or immunometric assays, also known as "two-site" or "sandwich" assays (see Chard, "Introduction to Radioimmune Assay and Related Techniques," in *Laboratory Techniques in Biochemistry and Molecular Biology*, North Holland Publishing Co., NY (1978)). In a typical immunometric assay, a quantity of unlabeled antibody is bound to a solid support that is insoluble in the fluid being tested, e.g., blood, plasma, urine, etc. After the initial binding of antigen to immobilized antibody, a quantity of detectably labeled second antibody (which, may or may not be the same as the first) is added to permit the detection and/or quantitation of bound antigen (see, e.g., *Radioimmune Assay Methods*, Kirkham, et al., ed. pp. 199-206 E&S Livingston, Edinburgh (1970)). Many variations of these types of assays are known in the art and may be employed for the detection of EDN.

In addition to the development of new antibodies and immunoassays for EDN, assays that have already been described in the art are suitable for use in the present method. Thus, the radioimmunoassay described in U.S. Pat. No. 5,928,883 may be used, as may the ELISA kit and EDN antibodies that are commercially available (Medical and Biological Laboratories Co., Ltd., Watertown, Mass.).

Although immunoassays are generally preferred, any other procedure that allows for the quantitation of EDN may also be employed. This includes immunoblotting assays, HPLC assays or the SELDI mass spectrographic procedure described more fully in the Examples section. In some instances, particularly where tissues are removed from a patient and examined, EDN levels may be determined based upon the amount of EDN mRNA present. This can be accomplished, for example, using the polymerase chain reaction in the presence of primers based upon the sequence shown in FIG. 2. Preferably, at least one of these primers includes the portion of the EDN sequence coding for the peptide of SEQ ID NO:3. The most important characteristic of all of the assays is that they be specific for the detection of EDN.

The selection of an appropriate control population whose samples will be compared with those derived from a test subject is routine for one of ordinary skill in the art of clinical assays. Controls may either be derived from the general population or selected from individuals believed to be disease free. Although not absolutely necessary, it is generally desirable to match the characteristics of controls and test subjects as closely as is practical. For example, it would generally be desirable for the control population to be of about the same age as the patient being tested. It should be recognized that once an EDN level has been established for the control population, it is not necessary to retest controls in each individual assay.

At a minimum, the conclusion that a subject is at increased risk of having or developing ovarian cancer requires that their levels of EDN be higher than those in the control samples to a degree that is statistically significant using standard scientific criteria. Based upon the results obtained using SELDI mass spectrometry, it is expected that the EDN level in patients with ovarian cancer will be at least five times higher than in patients that are free from ovarian disease. However, depending upon the particular assay used, different cutoff points for concluding that a patient is at risk may be used. For example, patients evidencing at least a 50% increase in levels relative to controls in an ELISA assay might be chosen for additional analysis and monitoring. Similarly, patients evidencing a twofold, fourfold or tenfold increase in EDN might be chosen.

Although assays of EDN have been established as being useful in the diagnosis of ovarian cancer, it is expected that these assays will also find use in helping to diagnose other types of cancer. Thus, for example, the assays may be used to screen patients for prostate cancer, breast cancer, or lung cancer. In each case, the same types of assays described above may be employed. In addition, the EDN assays may be combined with other assays that suggest the presence of cancer. For example, in the case of prostate cancer, EDN assays may be used in conjunction with assays of PSA. Similarly, subjects being tested for ovarian cancer may be tested both for EDN levels as well as for levels of CA 125. By combining several diagnostic tools, a more complete assessment of a subject can be made.

EXAMPLES

In the present Example, mass spectrometry-based protein chip profiling on urine samples collected from pre-operative ovarian cancer patients and age-matched healthy controls is used to identify and characterize candidate biomarkers associated with ovarian cancers.

A. Materials and Methods:

Urine Sample Collection and Processing

All patient-related biologic specimens were collected and archived under protocols approved by the Human Subjects Committees of the Partners HealthCare System, Boston, Mass. Urine samples were collected pre-operatively from the women requiring surgery for a "pelvic mass," at Brigham and Women's Hospital (BWH) and Massachusetts General Hospital (MGH). We randomly collected urine specimens from 84 post-menopausal women before surgery; 55 of them proved to have epithelial ovarian cancer, 29 had benign gynecologic tumor. A total of 88 age-matched urine specimens were also available from normal healthy women selected from the general population from Massachusetts General Hospital (MGH). The fresh collected urine in sterile tubes was processed within 8 hours and stored in aliquots at −80° C.

Mass Spectrometry Profiling of Urinary Proteins

Upon thawing, urine samples were thoroughly mixed and then centrifuged at 12,000 rpm at 4° C. for 5 min. The protein chip WCX2 (weak cation exchange, Ciphergen Biosystem, Fremont, Calif.) was activated by pretreatment with 10 mM of HCl for 5 min. The chip was then washed twice with 200 μl binding buffer (100 mM ammonium acetate, pH. 6.5) for each spot on the bio-processor. Fifty micro-liters of urine samples were directly applied on the spot surface and the chip was inserted into a bioprocessor for incubation on the mini-shaker (IKA-Work Inc. Wilmington, N.C.) at 600 rpm, at room temperature for 1 hour. After two washes with 350 μl of the binding buffer, the air-dried arrays were treated with saturated 3,5-dimethoxy-4-hydroxyinnamic acid (sinapinic acid) in 0.5% TFA (trifluoroacetic acid) and 50% acetonitrile before being analyzed by surface enhanced laser desorption/ionization time-of-flight mass spectrometry (SELDI-TOF-MS) (Protein Biology System II, Ciphergen Biosystems, Fremont, Calif.). The setting of mass resolution, accuracy, calibration, and shooting has been previously described (Ye, et al., *Clin Cancer Res.* 9:2904-2911 (2003)).

Protein Purification and Identification

A 3 ml urine sample from a patient with documented ovarian cancer and having the protein pattern of interest (higher intensity at peak of 8.7 and 17.4 kDa on SELDI-MS profile) was filtered through a 0.45 μm membrane and mixed with an equal volume of PBS buffer containing 1.0% 3-[(3-cholamidopropyl) dimethylammonio]-1-propanesulfonate (CHAPS), and 8 M urea. The sample was then applied to a Sephadex G-25 column for desalting and removal of the insoluble fraction. A 1.0 ml HiTrap™ CM-FF ion exchange column (Amersham Pharmacia Biotech AB, Uppsala, Sweden) was utilized for purification according to the provided protocol. Elution buffers containing 100 mM ammonium acetate (pH 6.0) and a gradient concentration of sodium chloride (0-1.0 M) were used. The eluted fractions of interest were subjected to SELDI-MS to confirm the presence of the desired protein peak and then separated by 10-20% gradient SDS-PAGE. The separated proteins were visualized by silver staining. The band of interest was excised from the gel and subjected to in-gel digestion with trypsin (Shevchenko, et al., *Anal Chem,* 68: 850-858, (1996)). The resultant polypeptides were further separated by liquid chromatography with online sequence analysis by tandem mass spectrometry (LC-MS/MS) (Mann, et al., *Ann. Rev. Biochem.* 70:437-473 (2001); Peng, et al., *J. Mass Spectrom.* 36:1083-1091 (2001)). The fragmentation ladders (the b and y ion series) from the lowest mass to the highest mass were used for the identification of the amino acid residues of the peptides and the protein identity was searched using a protein database.

Immunoassays and ELISA Quantification

Western blotting: A total of 6 μg of urinary protein prepared by acetone precipitation from normal and cancer patients was subjected to 12% SDS-PAGE separation. Proteins were transferred to a PVDF membrane and then 5% (w/v) of fat-free milk in TBST (10 mM Tris.HCl/100 mM NaCl/0.1% (v/v) Tween-20, pH 7.5) was used for blocking overnight at 4° C. A polyclonal antibody against human EDN was used for the primary reaction at a 1:300 dilution in TBST with 5% (w/v) fat-free milk for 2 hours. The membrane was then washed three times with Tris Buffered Saline-Tween-20 (TBST) for 15 min per wash. The secondary antibody was an anti-rabbit IgG coupled to horseradish peroxidase used according to a protocol for enhanced chemiluminescent detection (ECL, Pierce).

Immuno-precipitation: A total of 400 μg of urine protein prepared from acetone precipitation was desalted using a Sephadex G-25 column, and incubated with 5 μl monoclonal anti-human EDN antibody (MBL International Inc, Japan) in the washing buffer (20 mM Tris-HCl, pH. 7.6, 150 mM NaCl, 1 mM $MgCl_2$, 0.5% NP-40 and 10% glycerol) for 2 hours at 4° C. Twenty microliters Protein G (Pierce Biotechnology Inc.) was added for antigen-antibody binding at 4° C. for overnight. The incubation mixture was centrifuged at 14000 rpm, 4° C. for 5 min. Precipitate pellets were washed three times with the above washing buffer by centrifugation. The immune-precipitated protein pellets were dissolved in 20 μl of protein sample buffer containing 187 mM Tris-HCl, pH 6.8, 30% glycerol, 15% β-mercaptoethanol and 9% SDS. After boiling for 5 min, the proteins were separated by 15% SDS-PAGE.

Enzyme-Linked Immunosorbent Assay (ELISA): The urinary EDN protein concentration was quantified by specific antibody based ELISA, according to the provided protocol (MBL International Inc. Japan). Urine samples were thawed and centrifuged at 5000 rpm at 4° C. and transferred to new tubes. The diluted 150 μl urine samples (1:50) and EDN standards (0, 0.6, 1.2, 2.4, 4.8, 10, 20, 40 ng/ml) were added into 96-well polyvinyl plates. Each sample (100 μl) was then transferred to the antibody-coated micro-well plates simultaneously using a multi-channel pipette followed by a 1-hour incubation at room temperature. After 4 washes with washing buffer, 100 μl of peroxidase conjugated anti-human EDN solution were added and followed by a 1 hour incubation. After another 4 washes, the substrates (mixture of o-phenylenediamine-HCl and hydrogen peroxide) were added to start the color reaction for 10 min at room temperature. The reaction was stopped by the addition of 2N sulfuric acid ($H_2SO_4$). Plates were read at 492 nm and concentrations of urine EDN were calculated from each standard curve. The serum EDN and urine eosinophil cationic protein (ECP) concentrations were measured by using commercial ELISA kits (MBL International Inc. Japan) according to the provided protocols.

Protein Glycosylation and Dimerization Assay

N-Glycanase™ (Peptide-N-Glycosidase F) and O-Glycanase™ (Prozyme Inco. San Leandro, Calif.) were applied to the urine protein sample for pretreatment according to the provided protocols, which include the addition of reaction buffer with 0.1% SDS and 50 mM β-mercaptoethanol, heating at 100° C. for 5 min, 0.75% of NP-40, and incubation with N-glycanase overnight at 37° C. After glycanase pretreatment, the protein sample was subjected to SDS-PAGE separation and western blotting to detect the EDN protein. The total urine protein or the immune precipitated proteins were separated on SDS-PAGE and followed by glyco-protein staining with Pro-Q® Emerald 300 (Molecular Probes, Eugene, Oreg.). The identical gels for western blot and for glycoprotein staining were used for identification of specific glyco-EDN protein bands on the staining gels. The non-specific monoclonal antibody of mouse anti-human haptoglobin (Sigma-Aldrich) antibody was applied as the negative control. A concentrated benign urine protein sample was used as an internal control to normalize the protein intensity of the individual blots. The western blots and stained gels were scanned using an Imaging Densitometer (Model GS-700) and analyzed with the Quantity One software (Bio-Rad). The relative intensities of EDN protein on western blots and glyco-staining gels were analyzed.

Urinary Creatinine and Protein Quantification

Concentrated urine protein samples were prepared by acetone precipitation. The total urine creatinine concentration was measured by using the Creatinine Companion assay kit (Exocell, Inco. Philadelphia, Pa.) according to the protocol provided. The total urine protein concentration was measured by the BCA assay using the kit provided from Pierce Biotechnology, Inc. (Rockford, Ill.).

Statistical Analysis

The urine cationic protein profiling data and the intensity of the protein peaks of interest from benign ovarian tumor patients, ovarian cancer patients, and normal controls were compared using Student's t-test. The EDN concentration of the urine and serum quantified by ELISA was normalized by total protein or creatinine concentration. The measurements were transformed to the logarithmic scale and t-tests were used to compare the distributions in ovarian cancers, ovarian benign tumors and age-matched normal controls. The log-transformed urine EDN concentrations from the non-mucinous cancer patients and normal controls were used to generate a receiver operating characteristic (ROC) curve and to assess sensitivity at a fixed specificity level. To validate the sensitivity estimate, "leave-one-out" cross-validation was used, whereby one observation is iteratively omitted to obtain urine EDN cut-point, which is then used to classify the omitted observation. To evaluate the relationship between EDN concentration and other relevant serum measurements, correlation coefficients were estimated and linear models were fit comparing: 1) log-transformed urine EDN concentration against log-transformed serum EDN; 2) log-transformed serum EDN concentrations against blood eosinophil; and 3) log-transformed CA125 measurements against log-transformed urine EDN.

B. Results

Figure 4:
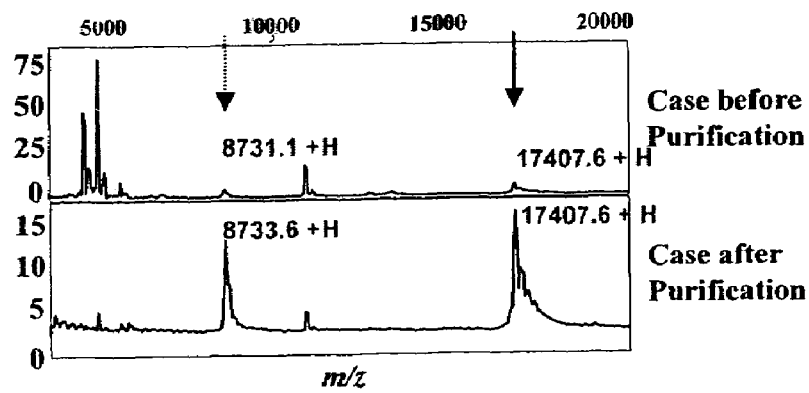
FIG. 4. Urine biomarker protein purification and mass spectrometry detection. The identical peak pattern of the peak at 8700 Da (dashed arrow) and 17400 Da (solid arrow) were present in a cancer case before (upper panel) and after HiTrap™ CM-FF ion exchange column purification (low panel).
Figure 5:
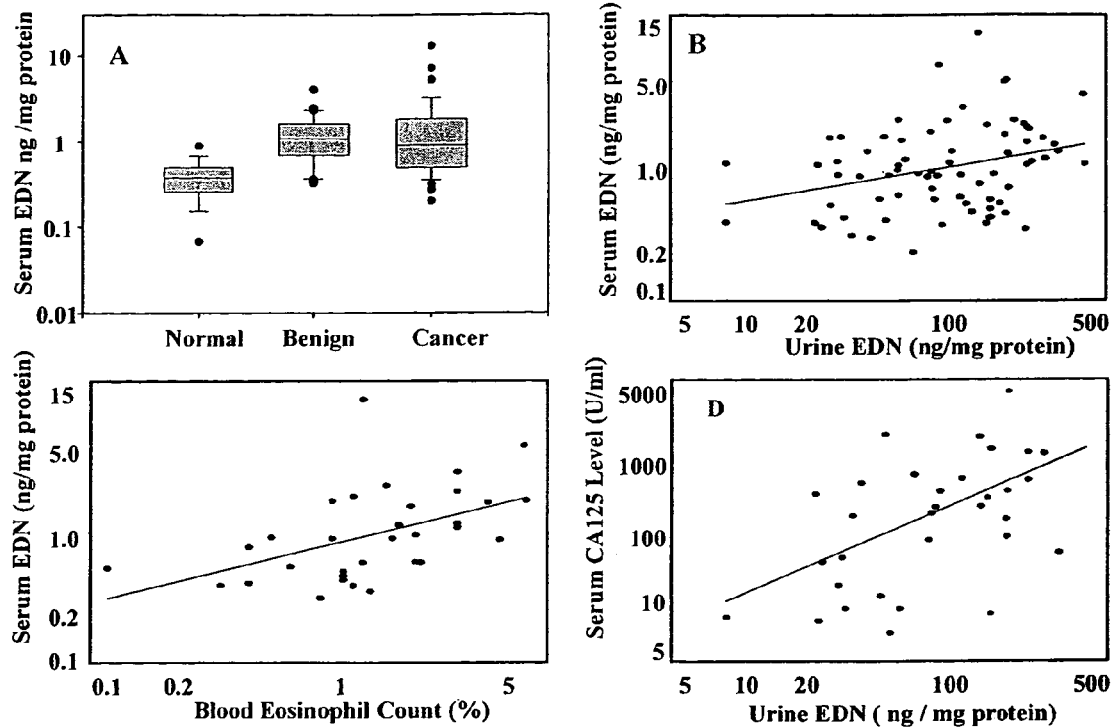
FIG. 5: A. Elevated total EDN protein in sera of ovarian cancer and benign tumor patients quantified by ELISA. The log-scale box-plot showed that EDN in urine from benign (n=29, mean=1.26) and cancer (n=55, mean=1.63) patients was significantly ($p<0.001$) greater than that of normal controls (n=30, mean=0.66) by ANOVA. B. The log-transformed urine and serum EDN concentration from benign and cancer patients was subjected to Pearson Correlation Coefficient analysis (n=73). C. The log-transformed blood eosinophil count (%) and serum EDN (ng per mg protein) concentration from the benign and cancer patients (n=32) was subjected to Pearson Correlation Coefficient analysis. D. The CA125 level (Unit per ml) and urine EDN (ng per mg protein) were log-transformed and subjected to Correlation Coefficient analysis (n=33).

Urinary Protein Mass-Spectrometry Profiling and Liquid Chromatography Purification To study the relevant cationic proteins in ovarian cancer urine specimens, we utilized the SELDI-TOF-MS to generate protein profiles using the weak-cationic exchange (WCX) surface chip. Two cationic protein peaks at 8730 and 17400 m/z were identified which had a significantly ($p<0.001$) higher peak intensity in benign ovarian tumor patients (7.72, n=29) and cancer patients (13.8, n=42) compared to normal controls (0.55, n=55) in the preliminary SELDI screening (FIG. 3). The candidate protein identified from cancer patients was purified using the cationic ion exchange chromatography. The eluted fractions were applied on SELDI-MS protein chip to confirm presence of the protein mass. Most of the urine proteins were removed from column purification steps and not detected by mass spectrometry. The enriched candidate urine cationic proteins were shown to have the identical mass spectrometry pattern as in the original screening profiles (FIG. 4). The purified cationic protein fraction was concentrated and separated on an 8-16% gradient SDS-gel and viewed by the silver staining. A lower band on the gel was observed with a molecular weight of ~17 kDa. In addition, an upper band was present indicating the presence of a second form of higher molecular weight (~35 kDa).

Eosinophil-Derived Neurotoxin (EDN): Identification, Characterization and Quantification The purified urine cationic protein was excised from the gel and subjected to trypsin digestion. The resultant peptides were further then subjected to LC-MS/MS for sequence analysis. Using this procedure, the cationic protein was identified as eosinophil-derived neurotoxin (EDN, also known as RNase 2) with the unique C-terminal peptide sequence, RDPPQYPVVPVHLDR (SEQ ID NO:3). The elevation of EDN in urine samples was confirmed by western blot and showed that EDN protein was elevated in the urine from cancer patients, with at least three different forms in the molecular weight range of 17-20 kDa, due primarily to glycosylation differences. To quantify the urine EDN, ELISAs were performed in 55 patients with ovarian cancer, 29 with benign ovarian tumor, and 88 age-matched healthy controls using a commercially available assay (MBL International Inc. Japan). EDN protein levels were normalized either by the total amount of urine protein or by urine creatinine concentration. The log-transformed mean of EDN concentration (ng per mg protein) in the urine of patients with benign ovarian tumor and cancer patients were 92.0 and 105.9 respectively, which was significantly different from the normal controls which had a mean value of 24.4 ($p<0.001$). A ROC curve illustrated the maximum specificity (94%) and sensitivity (72.2%) of urine EDN to separate the cancer cases from the normal controls. However, eosinophil cationic protein (ECP), another eosinophil ribonuclease with 67% amino acid sequence homology to EDN, was not present in the urine of cancer patient or in normal controls either by SELDI mass spectrometry profiling or by ELISA quantification.

The mean value of urine EDN protein and 95% confidence interval (CI) of patients with benign ovarian tumor (92, 61.0-138.6) and ovarian cancer (105.9, 85.5-131.1) were significantly different ($p<0.001$) from that in normal controls (24.2, 20.7-28.4) (Table 1). The total urine EDN protein concentration in benign ovarian tumor was not significantly different from the ovarian cancers. In addition, among all subtypes of ovarian cancers, the mucinous subtype was shown to have the lowest levels of urine EDN. Using 94% specificity as cutoff (75 ng/mg protein), urine EDN levels in the early stages of ovarian cancer (72.2% sensitivity) was comparable to that in the late stages of ovarian cancers (69% sensitivity). The non-mucinous ovarian cancer patients can be detected with 82.3% sensitivity (Table 1).

Coordinate Elevated Blood Eosinophil, Serum EDN, CA125 and Urine EDN in Ovarian Cancer Patients The elevated EDN level in the urine of ovarian cancer patients may be associated with an elevated serum EDN level and blood eosinophil count, as opposed to EDN synthesis from ovarian cancer cells directly. To test this hypothesis, serum EDN levels were measured with the above commercial available ELISA kit using a standard protocol. The log transformed mean values of serum EDN (ng/mg protein) from the benign ovarian tumor patients and ovarian cancer patients were 1.26 and 1.63, respectively, and significantly ($p<0.001$) higher than that in the controls (mean value=0.66 ng/mg protein). The increased urine EDN has a strong correlation tendency with the elevated serum EDN (n=73, correlation coefficient: r=0.298, p=0.0105). The possible correlation of elevated serum EDN with the increased blood eosinophil level was further tested. The combined blood eosinophil count percentile data of the benign ovarian tumor and cancer patients collected from our clinical database was plotted with their serum EDN concentration (ng/mg protein) in log-transformed scale. It clearly indicated that the increased incidence of high EDN level in serum was strongly correlated with blood eosinophil count (n=32, correlation coefficient: r=0.485, p=0.0049). Interestingly, the increased serum CA125 level was significantly correlated with the increased urine EDN in the benign and ovarian cancer patients (n=35, correlation coefficient: r=0.458, p=0.0074).

Hyperglycosylated EDN in Ovarian Cancer

Figure 6:
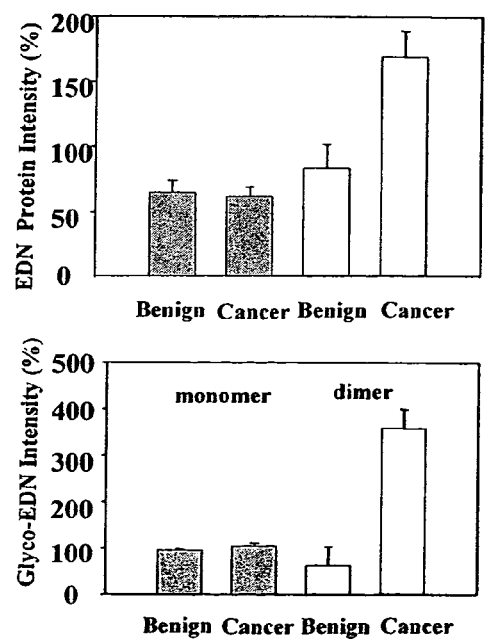
FIG. 6. Differential glycosylation patterns of EDN dimer in urine from ovarian benign and malignant cancer patients. A. Summarized relative protein intensity (the control benign sample as 100%) of high mobility, minimally glycosylated (solid boxes) and high mobility, hyperglycosylated forms of EDN (open boxes) from urine of benign and cancer patients. B. Summarized relative glycosylation intensities of the minimally glycosylated (solid boxes) and the hyperglycosylated forms of EDN (open boxes) in urine of benign and cancer patients.

The polypeptide sequence of EDN contains 5 potential sites for N-linked glycosylation. To evaluate whether the higher molecular weight form of EDN found in urine from benign ovarian tumor and cancer patients resulted from glycosylation, N-glycanase or O-glycanase was used to remove all potential glycosyl groups from the EDN polypeptide. After pretreatment with 0.1% SDS, 50 mM β-mercaptoethanol, 0.75% NP-40, with either N-glycanase, or O-glycanase (ProZyme, Inc. San Leandro, Calif.) incubation at 37° C. overnight, western blots showed that the high molecular weight, lower mobility, hyperglycosylated form of EDN disappeared and transformed to the lower molecular weight, high mobility form. The lower molecular weight, high mobility form of EDN was also slightly shifted to an even smaller size by glycanase treatment. This indicated that the mature monomer EDN was likewise slightly, or minimally glycosylated. Pretreatment control conditions (without glycanase) caused partial transformation of the glycosylated form of EDN. To further differentiate EDN in ovarian cancer and benign tumor patients, immune precipitation was used to purify EDN from the pooled urine specimen of the benign tumor (n=9) and cancer patients (n=12). A western blot showed that the immune precipitated hyperglycosylated form of EDN (upper band in gels) has a greater intensity in the cancer patients than that of the benign tumor patients. The minimally glycosylated form of EDN (lower band in gels) however, was shown to have similar intensities in the cancer and benign patients. The identical gel was also used for glycosylation staining. Interestingly, hyperglycosylated EDN was shown with much greater intensity in the cancer patients than that in benign tumor patients. There was no detectable difference in glycosylation intensity of the lower molecular weight form of EDN. The increased hyperglycosylated EDN protein intensity in urine of ovarian cancer patients was shown on the western blots, but much less difference for the lower molecular weight, minimally glycosylated form of EDN. The relative abundance of the minimally and the hyperglycosylated forms EDN of 9 benign tumor and 12 cancer patients is summarized in FIG. 6. The hyperglycosylated EDN was about 2-fold higher (p<0.001) in cancer urine after normalized with the total urine protein. This finding is consistent with our SELDI-mass profiling data that peak intensity of 17.4 kDa was 2-fold higher in urine of cancer patients than that in benign tumor likely due to enhanced chip surface binding of glycosylated form of EDN. However, the relative glycosylation-intensity of the hyperglycosylated EDN was ~6 times higher (p<0.001) in ovarian cancer urine than that from the benign patients. There was less detectable difference of the glycosylation intensity of minimally glycosylated EDN between the benign and malignant cancer patients.

C. Discussion

Eosinophils are rare granulocytes that are normally associated with allergic diseases or response to inflammation due to various parasitic infections and immune reactions. However, many types of human cancers are associated with extensive eosinophilia within the tumor tissue (Schwartz, R., *N. Engl. J. Med.* 348:1199-1200 (2003); Samoszuk, M. *Histol. Histopathol.* 12:807-812 (1997)), which include oral squamous cell carcinomas (Dorta, et al., *Histopathology* 41:152-157 (2002)), skin (Suster, S. *Semin. Diagn. Pathol.* 16:162-177 (1999)), breast (Pastrnak, et al., *Neoplasma* 31:323-326 (1984); Ali, et al, *Am. J. Pathol.* 157:313-321 (2000)), lung (Kodama, et al., *Cancer* 54:2313-2317 (1984)), and colorectal (Fernandez-Acenero, et al. *Cancer* 88:1544-1548 (2000)). The present Example demonstrates a significant (p<0.001) increase of urine EDN in ovarian cancer patients and correlation with the increased levels of blood eosinophil and serum EDN. It may be that the elevated urine EDN is not derived from ovarian cancer cells, but rather from the indirect pathological and immune reactions, which may include the eosinophil activation and degranulation. By using autofluorescence and immunohistochemistry, Samoszuk's group has shown the presence and degranulation of eosinophils in breast and ovarian cancer tissues (Samoszuk, et al., *Clin. Cancer Res.* 2:1867-1871 (1996); Samoszuk, et al., *Am. J. Pathol.* 148:701-706 (1996)) and in endometriosis (Blumenthal, et al. *Am. J. Pathol.* 156:1581-1588 (2000)). This observation may be relevant to our finding that EDN is especially apparent in women with endometrioid types of ovarian cancer and endometriomas (12 of 14 patients, Table 1).

EDN is a pyrimidine specific nuclease of the RNase A gene superfamily, also known as RNase 2, and it possesses several characterized biological activities. EDN is a major component of human eosinophilic leukocytes. Increased serum ribonuclease activity has been reported in women with ovarian carcinoma (Schleich, et al., *J. Cancer Res. Clin. Oncol.* 113:603-607 (1987)). But it was not clear if the high level of RNase activity is due to the elevation of EDN in serum because the EDN has >1000-fold RNase activity than other members of RNase proteins. Intact eosinophils as well as the "footprints" of cell undergoing degranulation were found in blood vessel adjacent to tumor in ovarian cancer (Samoszuk, M. *Histol. Histopathol.* 12:807-812 (1997)). Interestingly, the post-translational modification with N-terminal extension of amino acid residues −4 to −1 of signal peptide EDN has inhibitory activity of oocyte maturation (Sakakibara, et al., *Chem. Pharm. Bull.* (Tokyo) 39:146-149 (1991)) and is predominantly present in pregnant women (Sakakibara, et al., *J. Biochem* (Tokyo) 111: 325-330 (1992)). These findings together with our data of elevation of urine EDN in ovarian cancer patients strongly suggest that the activated eosinophil and EDN modification might cause abnormal ovarian functions.

We have further shown that the urine from ovarian cancer patients has about 6 times more hyperglycosylated EDN than urine from patients with benign ovarian tumor patients. Recent novel discoveries have shown that cancer malignancy is linked with protein glycosylation via the inhibition of apoptosis signaling pathway (Hakomori, et al., *Proc. Nat'l Acad. Sci. USA* 99:10231-10233 (2002); Kakugawa, et al., *Proc. Nat'l Acad. Sci. USA* 99:10718-10723 (2002); Alper, J., *Science* 301:159-160 (2003)). We suggest that post-translational modifications including glycosylation of EDN might play essential roles in ovarian cancer development. The complexity of EDN glycosylation may include the glycan types, structure and glycan binding sites. With a clear understanding of the biochemical properties of glycosylated EDN from the ovarian cancer patients, we could generate more specific antibodies to improve specificity and sensitivity for the urine test and to have better understanding of eosinophil related pathways in ovarian cancers.

TABLE 1

Comparison of clinical characteristics and urine eosinophil-derived neurotoxin (EDN) in ovarian benign, cancer patients and the age-matched normal postmenopausal controls.

| Characteristic | Patients | Eosinophil-Derived Neurotoxin (ng/mg protein) | | | | p-value |
| --- | --- | --- | --- | --- | --- | --- |
| | | Mean | 95% CI | Range | Positive (%) | |
| Normal | | | | | | |
| Total | 88 | 24.2 | 20.7-28.4 | 6.4-112.4 | 5 | |
| Benign | | | | | | |
| Serous cystadenoma | 6 | 89.6 | 25.2-319.0 | 22.7-350.5 | 40 | |
| Endometrosis | 3 | 129.0 | 27.6-602.4 | 79.3-259.4 | 75 | |
| Mucinous | 2 | 94.6 | 0.2-58227.9 | 57.1-156.8 | 50 | |
| Other | 18 | 87.4 | 48.6-157.1 | 7.9-465.2 | 72 | |
| Total | 29 | 92.0 | 61.0-138.6 | 7.9-465.3 | 66 | <0.001 |
| Ovarian Cancer Histotype | | | | | | |
| Serous | 40 | 113.1 | 90.3-141.7 | 26.2-377.1 | 72 | |
| Endometroid | 3 | 96.7 | 20.6-454.6 | 57.2-192.5 | 67 | |
| Mucinous | 5 | 52.5 | 24.3-113.4 | 28.5-147.4 | 20 | |
| Other | 8 | 132.5 | 55.0-319.2 | 21.9-475.6 | 73 | |
| Non-mucinous | 51 | 114.9 | 93.0-141.8 | 21.9-475.6 | 74 | <0.001 |
| Stage (non-mucinous) | | | | | | |
| I-II | 22 | 95.1 | 68.2-132.7 | 28.5-245.9 | 72.2 | <0.001 |
| III-IV | 31 | 112.9 | 84.2-151.6 | 21.9-475.6 | 69 | <0.001 |
| Total | 55 | 107.1 | 87.2-131.6 | 21.9-475.6 | 66 | <0.001 |

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A method of determining whether a human female subject is at increased risk of having ovarian cancer relative to the general population, comprising:
   (a) obtaining a test biological sample of urine from said subject;
   (b) determining the amount of eosinophil-derived neurotoxin (EDN) in said test biological sample wherein said EDN is characterized by the amino acid sequence of SEQ ID NO:1;
   (c) comparing the amount of EDN determined in step (b) with the amount in one or more control biological samples of urine; and
   (d) concluding that said subject is at increased risk of having ovarian cancer relative to the general population if the amount of EDN in said test biological sample is at least 20% higher than in said control biological samples.

2. The method of claim 1, wherein the determination of EDN amount is accomplished using an immunoassay.

3. The method of claim 1, wherein the amount of EDN is determined by mass spectrometry.

4. The method of claim 1, wherein the amount of EDN is determined by surface enhanced laser desorption/ionization mass spectrometry.

5. The method of any one of claims 1 or 2-4, wherein said subject is selected for testing based upon a clinical determination that she is at an elevated risk of having or developing ovarian cancer.

* * * * *

SEQUENCE LISTING

<160> NUMBER OF SEQ ID NOS: 3

<210> SEQ ID NO 1
<211> LENGTH: 161
<212> TYPE: PRT
<213> ORGANISM: Homo sapiens

<400> SEQUENCE: 1

```
Met Val Pro Lys Leu Phe Thr Ser Gln Ile Cys Leu Leu Leu Leu Leu
1               5                   10                  15

Gly Leu Leu Ala Val Glu Gly Ser Leu His Val Lys Pro Pro Gln Phe
            20                  25                  30

Thr Trp Ala Gln Trp Phe Glu Thr Gln His Ile Asn Met Thr Ser Gln
        35                  40                  45

Gln Cys Thr Asn Ala Met Gln Val Ile Asn Asn Tyr Gln Arg Arg Cys
    50                  55                  60

Lys Asn Gln Asn Thr Phe Leu Leu Thr Thr Phe Ala Asn Val Val Asn
65                  70                  75                  80

Val Cys Gly Asn Pro Asn Met Thr Cys Pro Ser Asn Lys Thr Arg Lys
                85                  90                  95

Asn Cys His His Ser Gly Ser Gln Val Pro Leu Ile His Cys Asn Leu
            100                 105                 110

Thr Thr Pro Ser Pro Gln Asn Ile Ser Asn Cys Arg Tyr Ala Gln Thr
        115                 120                 125
```

```
Pro Ala Asn Met Phe Tyr Ile Val Ala Cys Asp Asn Arg Asp Gln Arg
    130                 135                 140

Arg Asp Pro Pro Gln Tyr Pro Val Val Pro Val His Leu Asp Arg Ile
145                 150                 155                 160

Ile

<210> SEQ ID NO 2
<211> LENGTH: 735
<212> TYPE: DNA
<213> ORGANISM: Homo sapiens

<400> SEQUENCE: 2 gctgccctg aacccagaa caaccagctg gatcagttct cacaggagct acaggccgga      60
gactgggaaa catggttcca aaactgttca cttcccaaat ttgtctgctt cttctgttgg   120
ggcttctggc tgtggagggc tcactccatg tcaaacctcc acagtttacc tgggctcaat   180
ggtttgaaac ccagcacatc aatatgacct cccagcaatg caccaatgca atgcaggtca   240
ttaacaatta tcaacggcga tgcaaaaacc aaaatacttt ccttcttaca acttttgcta   300
acgtagttaa tgtttgtggt aacccaaata tgacctgtcc tagtaacaaa actcgcaaaa   360
attgtcacca cagtggaagc caggtgcctt taatccactg taacctcaca actccaagtc   420
cacagaatat ttcaaactgc aggtatgcgc agacaccagc aaacatgttc tatatagttg   480
catgtgacaa cagagatcaa cgacgagacc ctccacagta tccggtggtt ccagttcacc   540
tggatagaat catctaagct cctgtatcag cactcctcat catcactcat ctgccaagct   600
cctcaatcat agccaagatc ccatctctcc atatactttg ggtatcagca tctgtcctca   660
tcagtctcca tacccttca gctttcctga gctgaagtgc cttgtgaacc ctgcaataaa    720
ctgctttgca aattc                                                   735

<210> SEQ ID NO 3
<211> LENGTH: 15
<212> TYPE: PRT
<213> ORGANISM: Homo sapiens

<400> SEQUENCE: 3

Arg Asp Pro Pro Gln Tyr Pro Val Val Pro Val His Leu Asp Arg
1               5                   10                  15
```